(12) United States Patent
Sorge et al.

(10) Patent No.: US 7,728,363 B2
(45) Date of Patent: Jun. 1, 2010

(54) PROTECTIVE STRUCTURE FOR SEMICONDUCTOR SENSORS

(75) Inventors: Stephan Sorge, Dresden (DE); Christian Kunath, Dresden (DE); Eberhard Kurth, Moritzburg (DE)

(73) Assignee: Fraunhofer-Gesellschaft zur Foerderung der angewandten Forschung e.V., Munich (DE)

( * ) Notice: Subject to any disclaimer, the term of this patent is extended or adjusted under 35 U.S.C. 154(b) by 225 days.

(21) Appl. No.: 11/936,962

(22) Filed: Nov. 8, 2007

(65) Prior Publication Data

US 2008/0111161 A1    May 15, 2008

(30) Foreign Application Priority Data

Nov. 9, 2006   (DE) .................. 10 2006 052 863

(51) Int. Cl.
*H01L 29/68* (2006.01)
(52) U.S. Cl. .................. 257/253; 257/E29.299
(58) Field of Classification Search ......... 257/252–253, 257/E29.299
See application file for complete search history.

(56) References Cited

U.S. PATENT DOCUMENTS

| 4,589,970 | A | | 5/1986 | Ligtenberg et al. |
| 4,816,888 | A | * | 3/1989 | Tanaka et al. ............... 257/253 |
| 4,849,798 | A | * | 7/1989 | Wantanabe .................. 257/253 |
| 5,407,854 | A | | 4/1995 | Baxter et al. |
| 5,414,284 | A | | 5/1995 | Baxter et al. |
| 6,316,716 | B1 | | 11/2001 | Hilgrath |
| 2005/0186697 | A1 | * | 8/2005 | Yang ........................... 438/49 |
| 2005/0263798 | A1 | * | 12/2005 | Kurth et al. .................. 257/253 |
| 2006/0102935 | A1 | * | 5/2006 | Yitzchaik et al. ............ 257/253 |
| 2008/0061323 | A1 | * | 3/2008 | Yazawa et al. ............... 257/253 |

FOREIGN PATENT DOCUMENTS

GB    1 229 385    4/1971

* cited by examiner

*Primary Examiner*—Allan R. Wilson
(74) *Attorney, Agent, or Firm*—Keating & Bennett, LLP

(57) ABSTRACT

A protective structure for a semiconductor sensor integrated in a semiconductor substrate for use in a state that is in direct contact with a measuring medium has a semiconducting layer that is applied to the semiconductor substrate, a metal layer and an insulating layer. The insulating layer is disposed between the semiconducting layer and the metal layer and electrically insulates same.

17 Claims, 2 Drawing Sheets

PROTECTIVE STRUCTURE FOR SEMICONDUCTOR SENSORS

This application claims priority from German Patent Application No. 102006052863.8, which was filed on Nov. 9, 2006, and is incorporated herein in its entirety by reference.

BACKGROUND OF THE INVENTION

1. Field of the Invention

The present invention relates to a protective structure for semiconductor sensors, and more particularly a monolithic MIS protective structure for semiconductor sensors.

2. Description of the Related Art

Sensors that are exposed to environmental influences in order to be able to detect measured quantities cannot in any case be protected from electric or electrostatic overstress as effectively as other semiconductor devices. Ion-sensitive field-effect transistors (ISFETs), for example, do not have a metallic gate at which protective structures could be realized. On the contrary, here the gate insulator lies functionally exposed in the channel area of the transistor and is thus vulnerable to electric damaging. Such negative influences are, for example, electrostatic discharges (ESD) or disallowed electrical operating conditions such as excess voltage, polarity inversion and the like.

Ion-sensitive field-effect transistors are used in the analysis of liquid media, for example. In these sensors, for example, a drain-source current is regulated through ions in a measuring medium having direct contact with the gate insulator and causing, depending on the ion charge, an electric field there that influences the drain-source current whereby the measuring medium can be analyzed. Therefore, these sensors are also referred to as field-effect based sensors. For a flawless mode of operation and for the stability of the gate insulator, it is important that these semiconductor sensors are protected from a discharge of static voltages and/or from disallowed electrical operating conditions such as polarity inversions.

Currently, voltage-sensitive sensor structures can be protected by allocating a structure to the sensor element that can incorporate, for example, p-n junctions or also capacitor elements. A substantial disadvantage of protective structures in the form of conventional p-n junctions is the relatively high leakage current, whereby a precise potentiometric measurement can be influenced negatively. On the other hand, capacitors are disadvantageous as protective structures to the effect that they are conducting for alternating currents (e.g. EMC stress) and do not provide effective protection from other disallowed operating cases (polarity inversion).

SUMMARY OF THE INVENTION

According to an embodiment, an integrated semiconductor sensor for use in a state that is in direct contact with a measuring medium may have: a semiconductor substrate with a first and a second doped trace region and a gap between the first and second trace regions, and an insulating layer that separates the semiconductor substrate along the gap from the measuring medium to form an ion-sensitive field-effect transistor; a semiconducting layer that is applied to the semiconductor substrate; a metal layer; and an insulating layer, wherein the insulating layer is disposed between the semiconducting layer and the metal layer and electrically insulates same.

Another embodiment may have a use of an integrated semiconductor sensor as a protection of the semiconductor sensor from an electrostatic discharge, the integrated semiconductor sensor having: a semiconductor substrate with a first and a second doped trace region and a gap between the first and second trace regions, and an insulating layer that separates the semiconductor substrate along the gap from the measuring medium to form an ion-sensitive field-effect transistor; a semiconducting layer that is applied to the semiconductor substrate; a metal layer; and an insulating layer, wherein the insulating layer is disposed between the semiconducting layer and the metal layer and electrically insulates same.

Another embodiment may have a use of an integrated semiconductor sensor as a protection of the semiconductor sensor from a polarity inversion and/or disallowed operating conditions, the integrated semiconductor sensor having: a semiconductor substrate with a first and a second doped trace region and a gap between the first and second trace regions, and an insulating layer that separates the semiconductor substrate along the gap from the measuring medium to form an ion-sensitive field-effect transistor; a semiconducting layer that is applied to the semiconductor substrate; a metal layer; and an insulating layer, wherein the insulating layer is disposed between the semiconducting layer and the metal layer and electrically insulates same.

The present invention is based on the finding that a semiconductor sensor or a field-effect based sensor structure on a substrate can be protected from electrostatic discharges and/or electrochemically unfavorable operating cases at a contact with a measuring medium by integrating a metal insulator semiconductor structure (MIS structure, MIS=metal insulator semiconductor) on the same substrate or die. According to the invention, a protective structure is thus integrated in a advantageously close spatial relation to the semiconductor sensor in the same substrate.

For a protection of the field-effect based sensor structure from ESD and/or for a protection of sensor-typical functional layers from electrochemically unfavorable operating cases, an MIS structure that is integrated in the same substrate/die as the sensor structure to be protected and that comprises the following layers and structures, respectively, is used as a protective sensor.

First, this is a strongly n- or p-doped region in or on the substrate ($n^+$- or $p^+$-conducting region/substrate). Thereon, for example, an epitactic layer with a complementary line type with a layer thickness $d_{epi}$ is located that forms a p-n junction with the underlying $n^+$- or $p^+$-conducting region. Following is an insulating layer lying thereon with a layer thickness $d_{iso}$ that may be in a range of, for example, 0.1 to 30 nm. Finally, the protective structure comprises a metal layer that is in a contact with the measuring medium during use of the semiconductor sensor, wherein the contact is ensured either via a bare unprotected surface or via a protective layer (e.g. an oxide layer) that is created or, as the case may be, deposited on the surface. The protective layer can either be created to protect, for example, the metal layer from the ions, or it forms natively (such as by the measuring medium acting upon the metal layer). To ensure a sensitivity that is as high as possible, it is advantageous to create a low-impedance contact between the measuring medium and the metal layer. This can be done, for example, through a choice of material for the metal layer that is adapted to the measuring medium or, as the case may be, through applying a protective layer that is adapted to the measuring medium.

The physical properties of the protective structure can now be adapted to the respective requirements by an adaptation or variation of the layer thicknesses, and particularly of the layer thickness of the insulating layer $d_{iso}$ and of the layer thickness of the epitactic layer $d_{epi}$, as well as by a suitable choice of material.

The choice of material for the metal and/or insulator or, as the case may be, the adaptation of the energetic barrier from the metal to the insulator in conjunction with the energetic band structure of the semiconductor influences the current-voltage characteristic of the structure in its magnitude as well as in its respective performance, in a positive and in a negative direction.

Depending on doping profiles, layer thicknesses and choice of material, the electrical performance of this structure may be adapted to the requirements. By a respective choice of material at a respective layer thickness $d_{iso}$ for the insulating layer, either a Schottky diode (when for example $d_{iso} < 1$ nm) or an MIS tunnel diode (1 nm $< d_{iso} < 5$ nm) or an MIS capacitance (for $d_{iso} > 5$ nm) forms between the metal layer and the semiconducting material. The layer thickness $d_{iso}$ can have various values, for example $d_{iso} < 50$ nm and advantageously $d_{iso} < 10$ nm.

By a variation of the layer thickness $d_{epi}$ of the epitactic semiconductor layer, an MIS switching diode can be created that may be operated in a high-impedance and in a low-impedance state. The high-impedance state reduces leakage currents in the operating case, i.e. in normal sensor operation. The leakage currents are considerably smaller with the protective structure according to the invention than with conventional p-n junctions. When a switching threshold is exceeded, such as when the acting voltage becomes too high, the diode passes from the high-impedance into the low-impedance state and enables increased electrical conductivity, whereby the semiconductor sensor is protected. The layer thickness $d_{epi}$ has a value of, for example, $0.1 < d_{epi} < 50$ µm, advantageously a value of $0.1 < d_{epi} < 15$ µm, more advantageously a value of $1 < d_{epi} < 15$ µm, and even more advantageous is $d_{epi} = 1 \ldots 10$ µm.

It is a major advantage of the present invention that the manufacture of the protective structure can be carried out by means of semiconductor processes and the semiconductor process compatibility as well as an environmental compatibility are ensured.

Furthermore, the present invention is advantageous particularly regarding the adaptability of the electric selectivity characteristic to the specific requirements. Worth mentioning is in particular a reduction of the leakage current in the measuring and in the operating case, respectively, and a high current-carrying capacity in the protecting case through a switching functionality of the structure to an on- and an off-state. Accordingly, the particular advantage of the present invention lies in an adjustably small leakage current and in a quick response and a high current-carrying capacity in the protecting case, with simultaneous monolithic integration of the semiconductor sensor and of the protective structure in a semiconductor substrate.

BRIEF DESCRIPTION OF THE DRAWINGS

Embodiments of the present invention will be detailed subsequently referring to the appended drawings, in which.

DETAILED DESCRIPTION OF THE PREFERRED EMBODIMENTS

Before the present invention will be discussed in the context of the drawings in more detail below, it is pointed out that like elements in the figures are provided with like or similar reference numbers and that a repeated description of these elements is omitted.

Figure 1:
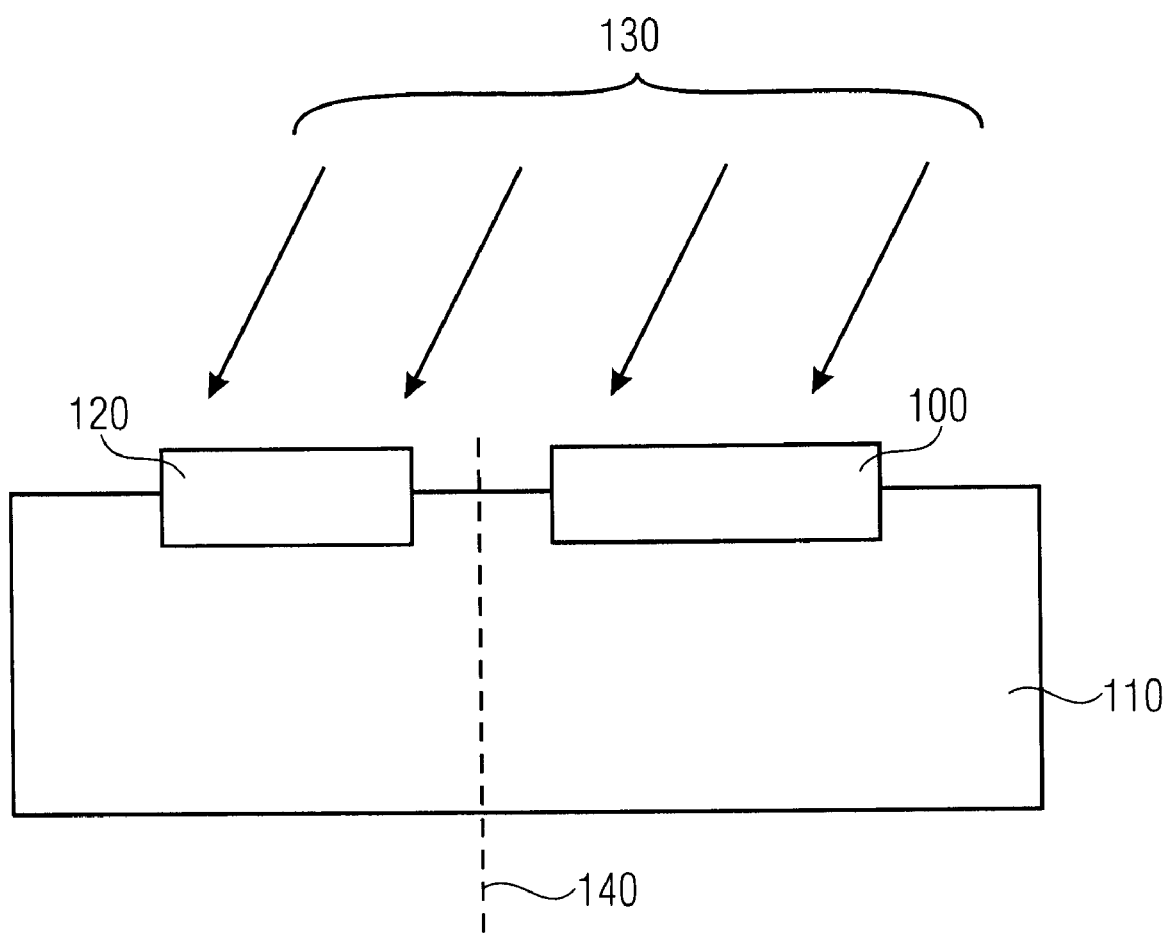
FIG. 1 shows a schematic circuit diagram of a monolithically integrated protective structure.

FIG. 1 shows a schematic representation of a protective structure 100 that is integrated on a substrate 110 along with a semiconductor sensor 120. The protective structure 100 as well as the semiconductor sensor 120 are exposed to a measuring medium 130. According to the invention, the protective structure 100 as well as the semiconductor sensor 120 are thus monolithically integrated in the substrate 110, wherein they are integrated, for example, in different regions of the substrate 110, which are separated in FIG. 1 by a dividing line 140. The dividing line 140 only serves as an illustration of a lateral integration of the protective structure 100 (next to the semiconductor sensor 120) on the same substrate 110 and does not imply a structural feature of the substrate 110.

Figure 2:
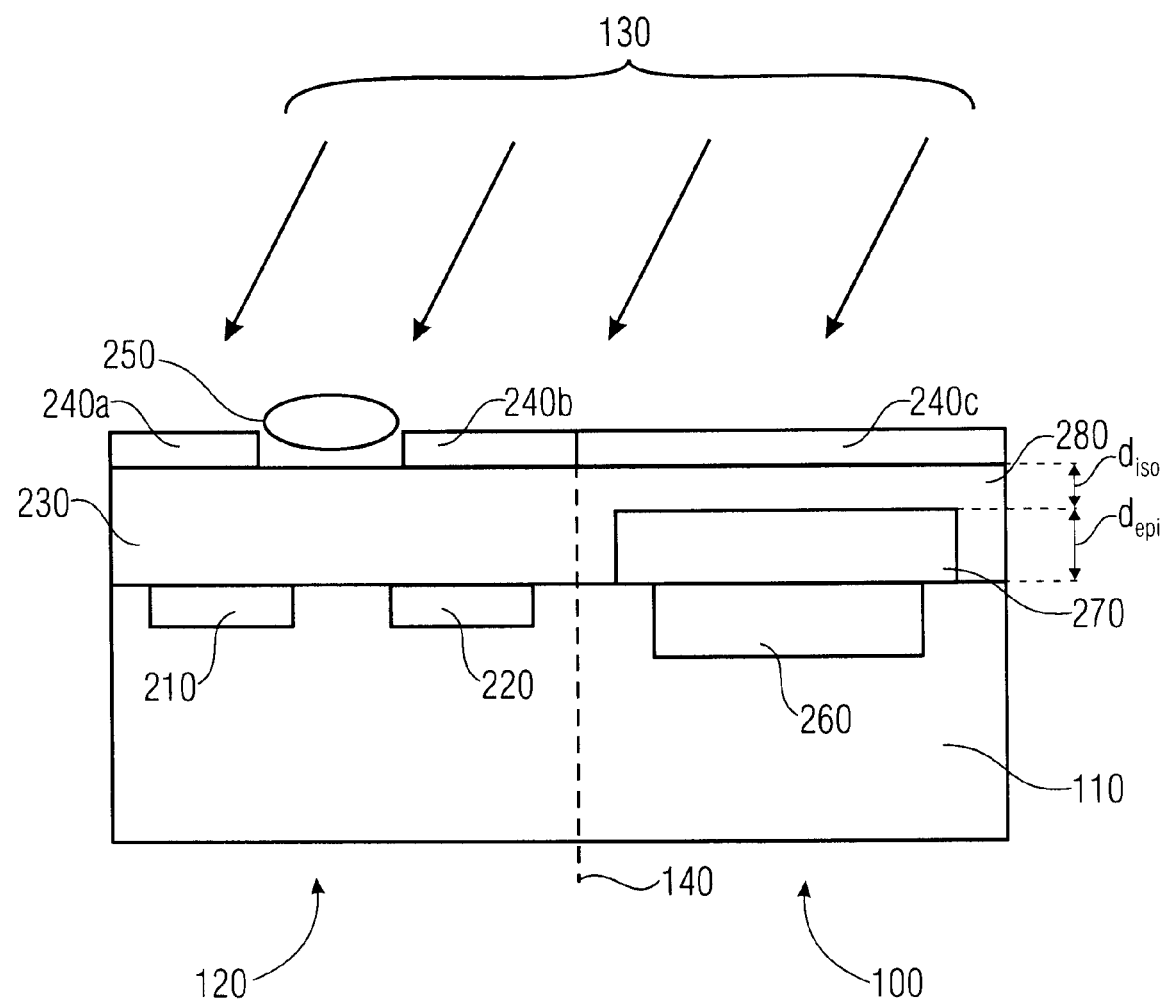
FIG. 2 shows a cross-sectional view of an ISFET sensor with an MIS protective structure.

FIG. 2 shows an embodiment wherein the semiconductor sensor 120 is given by an ISFET sensor and the protective structure 100 comprises an MIS layer structure, wherein the semiconductor sensor 120 and the protective structure 100 are again represented as separated by the dividing line 140. The semiconductor sensor 120 as well as the protective structure 100 are again exposed to the measuring medium 130, which acts from above in the chosen way of illustration.

The semiconductor sensor 120 that is integrated in the substrate 110 comprises a first doped trace region 210 and a second doped trace region 220. The first and second doped trace regions 210, 220, respectively, that are embedded in the substrate 110, are, for example, a source or, as the case may be, a drain terminal of the ISFET sensor 120. Subsequently, the ISFET sensor 120 comprises an insulating layer 230 on which, finally, a first metal layer 240a and a second metal layer 240b are deposited that leave a gap 250 vacant. The first and second doped trace regions 210, 220 and the first and second metal layers 240a, 240b are disposed in such a way that the gap 250 substantially corresponds to a region between the first and second trace regions 210, 220. In a conventional field-effect transistor the gate electrode is attached at the gap 250. In the semiconductor sensor 120, this gap 250 lies exposed, whereby the measuring medium 130 is separated from the substrate 110 only by the insulating layer 230, along the gap 250. In the operating case, for example, ions of the measuring medium 130 create an electric field in the gap 250 that influences an electric signal between the first and second trace regions 210, 220, and thus the measuring medium 130 can be analyzed.

In an adjacent region of the substrate 110 that is separated by the dividing line 140, the protective structure 100 is located, which in this embodiment is given by an MIS layer structure. It comprises, for example, a substrate area 260 in which a substrate doping for the MIS structure 100 is carried out. Thereon, an epitactic, semiconducting layer 270 with a layer thickness $d_{epi}$ is deposited. This epitactic, semiconducting layer 270 and the substrate 110 are separated from a terminal third metal layer 240c by an insulating layer 280. Between the third metal layer 240c and the epitactic, semiconducting layer 270, the insulating layer 280 has a layer thickness $d_{iso}$. The dividing line 140 is also to indicate that the protective structure 100 is integrated next to the semiconductor sensor 120 in the substrate 110.

In the monolithic integration of the protective structure 100 and the semiconductor sensor structure 120, involved layers may comprise like materials or, as the case may be, may have been applied as one layer. For example, the two insulating layers 230 and 280 can be a grown layer or, as the case may be, the first, second and third metal layers 240a, 240b, 240c can comprise a like material and can have been applied simultaneously. Furthermore, the first, second and/or third metal layers 240a, 240b, 240c optionally can comprise a protective layer (e.g. an oxide layer) that was either created artificially, or, as the case may be, forms naturally by an acting of the measuring medium 130. Applying the protective layer to the first, second and/or third metal layers 240a, 240b and 240c is advantageous particularly to the effect that thereby, a pinpoint protection of the first, second and/or third metal layers 240a, 240b and 240c can be achieved and/or the impedance of the contact of the third metal layer 240c with the measuring medium 130 can be set correspondingly low. For example, noble metals, metals of the transition elements or metals suitable due to their chemical stability can be used as materials for the metal layers 240a, 240b and 240c.

Advantageously, the substrate doping exhibits a substantially stronger doping in the substrate area 260 than in the epitactic, semiconducting layer 270 and, furthermore, is of a complementary line type. Depending on the chosen doping for the substrate area 260, i.e. either a $p^+$- or $n^+$-doping, the MIS protective structure 100 is in the state of forward and reverse direction, respectively, depending on the voltage compared to the measuring medium 130.

To conclude, various aspects of the present invention can be summarized as follows. An MIS protective structure 100 comprises a metal insulator semiconductor structure (subsequently referred to as MIS structure) that is integrated on the same substrate 110 as the structure to be protected (i.e. the semiconductor sensor element 120). The MIS structure 100 can further be characterized by the metal electrode 240c having a low-impedance contact with the solutions that are to be measured (i.e. of the measuring medium 130).

Regarding the layer thicknesses, the following ranges are possible. The insulating layer 280 between the semiconducting structure 110 and the first and second metal electrodes 240a, 240b can have a layer thickness $d_{iso}$ from 0.1 to 10 nm, and the epitactic, semiconducting layer 270 can have a layer thickness $d_{epi}$ from 0.01 to 50 μm and advantageously from 0.1 to 10 μm.

The doping of the individual layers can be chosen as follows, for example. The epitactic layer 270 of the MIS structure 100 can comprise, for example, a doping of up to $10^{18}$ and that of the substrate area 260 a doping of up to $10^{21}$ Finally, the doping of the substrate area 260 can comprise an inverse channel type compared to the doping of the epitactic layer 270.

The protective structure 100 for the semiconductor sensor 120 according to the invention thus is advantageous particularly to the effect that with a suitable dimensioning, a switching performance between a high-impedance state in the measuring case and a low-impedance state in the protecting case can be achieved. Through a variation of materials, layer thicknesses and doping profiles, a flexible adaptation to concrete requirements is achievable. Thus, the MIS structure 100 offers a protection of the sensor structure 120 from negative influences such as electrostatic discharges (ESD) or from disallowed electrical operating conditions (polarity inversion).

In embodiments of the present invention, the ESD protection of an ISFET 120 is inventively realized in the same substrate 110 by means of an MIS diode 120. Thus, the MIS diode 120 serves as a protective element for potentiometric sensors, according to the invention.

While this invention has been described in terms of several embodiments, there are alterations, permutations, and equivalents which fall within the scope of this invention. It should also be noted that there are many alternative ways of implementing the methods and compositions of the present invention. It is therefore intended that the following appended claims be interpreted as including all such alterations, permutations and equivalents as fall within the true spirit and scope of the present invention.

What is claimed is:

1. An integrated semiconductor sensor for use in a state that is in direct contact with a measuring medium, comprising:
    a semiconductor substrate with a first and a second doped trace region and a gap between the first and second trace regions, and a first insulating layer that separates the semiconductor substrate along the gap from the measuring medium to define an ion-sensitive field-effect transistor;
    a semiconducting layer that is applied to the semiconductor substrate;
    a metal layer; and
    a second insulating layer comprising a layer thickness $d_{iso}$ between 0.1 nm and 50 nm,
    wherein the second insulating layer is disposed between the semiconducting layer and the metal layer and electrically insulates same.

2. The integrated semiconductor sensor according to claim 1, wherein the metal layer comprises a face turned away from the second insulating layer, in order to be able to be brought into contact with the measuring medium via a protective layer or directly.

3. The integrated semiconductor sensor according to claim 2, wherein the protective layer comprises an oxide layer.

4. The integrated semiconductor sensor according to claim 1, wherein a protective layer is formed on the metal layer such that the contact with the measuring medium is of low impedance.

5. The integrated semiconductor sensor according to claim 1, wherein the layer thickness $d_{iso}$ of the second insulating layer is between 0.1 nm and 10 nm.

6. The integrated semiconductor sensor according to claim 1, wherein the semiconducting layer comprises a layer thickness $d_{epi}$ between 0.1 and 50 μm, and $d_{epi}$ is advantageously in a range from 0.1 to 10 μm.

7. The integrated semiconductor sensor according to claim 1, wherein the semiconducting layer includes an epitactic semiconducting layer on the semiconductor substrate.

8. The integrated semiconductor sensor according to claim 1, wherein the semiconducting layer comprises a doping of up to $10^{18}$ per $cm^3$.

9. The integrated semiconductor sensor according to claim 1, wherein the semiconductor substrate further comprises a substrate area with a doping higher than that of the semiconducting layer, and the substrate area is in contact with the semiconducting layer.

10. The integrated semiconductor sensor according to claim 9, wherein the substrate area comprises a doping of up to $10^{21}$ per $cm^3$.

11. The integrated semiconductor sensor according to claim 9, wherein the semiconducting layer is n-conducting and the substrate area is $p^+$-conducting or the semiconducting layer is p-conducting and the substrate area is $n^+$-conducting.

12. The integrated semiconductor sensor according to claim 1, wherein the semiconductor layer, the metal layer, and the second insulating layer define a protective structure laterally separated from the ion-sensitive field-effect transistor.

13. The integrated semiconductor sensor according to claim 1, wherein the metal layer, the semiconducting layer and the second insulating layer are arranged to define a Schottky diode.

14. The integrated semiconductor sensor according to claim 1, wherein the metal layer, the semiconducting layer and the second insulating layer are arranged to define an MIS tunnel diode.

15. The integrated semiconductor sensor according to claim 1, wherein the metal layer, the semiconducting layer and the second insulating layer are arranged to define an MIS capacitance.

16. A use of an integrated semiconductor sensor as a protection of the semiconductor sensor from an electrostatic discharge, the integrated semiconductor sensor comprising:
   a semiconductor substrate with a first and a second doped trace region and a gap between the first and second trace regions, and a first insulating layer that separates the semiconductor substrate along the gap from the measuring medium to define an ion-sensitive field-effect transistor;
   a semiconducting layer that is applied to the semiconductor substrate;
   a metal layer; and
   a second insulating layer comprising a layer thickness $d_{iso}$ between 0.1 nm and 50 nm,
   wherein the second insulating layer is disposed between the semiconducting layer and the metal layer and electrically insulates the semiconducting layer and the metal layer.

17. A use of an integrated semiconductor sensor as a protection of the semiconductor sensor from a polarity inversion and/or disallowed operating conditions, the integrated semiconductor sensor comprising:
   a semiconductor substrate with a first and a second doped trace region and a gap between the first and second trace regions, and a first insulating layer that separates the semiconductor substrate along the gap from the measuring medium to define an ion-sensitive field-effect transistor;
   a semiconducting layer that is applied to the semiconductor substrate;
   a metal layer; and
   a second insulating layer comprising a layer thickness $d_{iso}$ between 0.1 nm and 50 nm,
   wherein the second insulating layer is disposed between the semiconducting layer and the metal layer and electrically insulates the semiconducting layer and the metal layer.

* * * * *